United States Patent [19]

Nonaka et al.

[11] 4,212,945
[45] Jul. 15, 1980

[54] PROCESS FOR RECOVERING PROTEASE

[75] Inventors: Yuji Nonaka; Kiyotaka Oyama; Heijiro Satoh, all of Shin-nanyo, Japan

[73] Assignees: (Zaidanhojin) Sagami Chemical Research Center; Toyo Soda Manufacturing Company, Limited, both of Tokyo, Japan

[21] Appl. No.: 907,006

[22] Filed: May 18, 1978

[30] Foreign Application Priority Data

May 23, 1977 [JP] Japan .................................. 52-58827

[51] Int. Cl.$^2$ .......................... C12N 9/48; C07G 7/02
[52] U.S. Cl. .................................... 435/212; 435/213; 435/218; 435/219; 435/225; 435/816; 435/70
[58] Field of Search ............... 195/29, 66 R; 435/212, 435/213, 218, 219, 225

[56] References Cited

U.S. PATENT DOCUMENTS

| | | | |
|---|---|---|---|
| 4,086,136 | 4/1978 | Isowa et al. ........................... | 195/29 |
| 4,119,493 | 10/1978 | Isowa et al. ........................... | 195/29 |

OTHER PUBLICATIONS

Perlman, Methods in Enzymology, vol. XIX, pp. 646–647, 688–693, 696–697, 758, 759 and 785, (1970).
Journal of Fermentation Technology, 40, 346–353, (1962).
Journal of Biological Chemistry, 212, 255–269, (1955).

Primary Examiner—Lionel M. Shapiro
Attorney, Agent, or Firm—Oblon, Fisher, Spivak, McClelland & Maier

[57] ABSTRACT

Protease is recovered by reacting a first amino acid whose amino group is protected with a protective group with a second amino acid whose carboxyl group is protected with a protective group, in an aqueous medium in the presence of a protease to result a peptide synthesis to deposit the addition compound of a dipeptide and said second C-terminal protected amino acid; dissolving said addition compound into the aqueous medium by adding a polar organic solvent which is miscible with water and separating an insoluble material from the resulting suspension by a solid-liquid separation to isolate the protease.

9 Claims, No Drawings

PROCESS FOR RECOVERING PROTEASE

BACKGROUND OF THE INVENTION

1. Field of the Invention

The present invention relates to a process for recovering protease. More particularly, it relates to a process for recovering protease by isolating the protease from an addition compound after a peptide synthesis of peptide-bonding amino acid derivatives in the presence of the protease.

2. Description of Prior Arts

It has been known that proteases such as papain and chymotrypsin are used for forming peptide bonds as the reverse reaction of protein decomposition. For example, anilides have been produced by using papain by Bergman and the peptide syntheses using monoaminocarboxylic acids such as leucine having N-terminal protective benzoyl group and leucine and glycine having C-terminal protective amide or anilide group have been attained with papain and chymotrypsin by Fruton. (Advances in Protein Chemistry Vol. 5, page 33 (1949). Academic Press Inc. New York, N.Y.).

Recently, some of the inventors Isowa et al. reported peptide syntheses using amino acids having an N-terminal protective benzyloxycarbonyl group and amino acids having a C-terminal ester group with enzymes such as papain, Prolisin, Subtilisin BPN' etc. (Nippon Kagakukai 35th Autumn Meeting Brief Report Pages 482 and 486 (1976) Nippon Kagakukai).

Some of the inventors and Isowa et al. proposed the reaction as asparatic acid or glutamic acid having N-terminal protective group with a monoaminomonocarboxylic acid having C-terminal protective group which has no other functional group in the presence of protease whereby an addition compound of the monoaminomonocarboxylic ester having no other functional group and the reaction product was formed, and the isolation of the addition product was carried out. (Japanese Patent Application No. 7279/1977; U.S. Pat. application No. 870,108; Canadian Pat. application No. 295,711 and West German Patent Application P 2801238.6).

The protease used in the process is considered to preserve the protease activity after the reaction. However, the filtrate of the reaction mixture from which the reaction product is separated (The reaction product is deposited to be insoluble in the medium for the reaction.) has only weak protease activity.

According to the studies of the inventors, it has been found that most of the protease used in the reaction is separated together with the reaction product from the filtrate and preserves the protease activity and can be reused for the peptide synthesis etc. after isolating the protease from the reaction mixture.

SUMMARY OF THE INVENTION

It is an object of the present invention to provide a process for recovering protease by isolating protease from a reaction product of a peptide synthesis in the presence of protease.

The foregoing and other objects of the present invention have been attained by providing a process for recovering protease which comprises reacting a first amino acid whose amino group is protected with a protective group with a second amino acid whose carboxyl group is protected with a protective group, in an aqueous medium in the presence of the protease to result a peptide synthesis and to deposit an addition compound of a dipeptide and said second C-terminal protected amino acid; dissolving the addition compound into the aqueous medium by adding a polar organic solvent which is miscible with water and separating an insoluble material from the resulting suspension by a solid-liquid separation to isolate the protease as the solid phase.

DETAILED DESCRIPTION OF THE PREFERRED EMBODIMENTS

The addition compounds are disclosed in the copending applications (USA Patent Application Ser. No. 870,108; Canada Pat. application No. 295,711 and West German Patent Application No. P.2801238.6) which are formed by an addition of the second C-terminal protected amino acid with a dipeptide of the first N-terminal protected amino acid and the second C-terminal protected amino acid.

The typical addition compounds have the formula

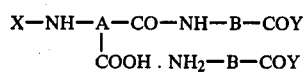

wherein A represents a residue of aspartic acid or glutamic acid excluding C-terminal and N-terminal and B represents a residue of the second amino acid excluding C-terminal or N-terminal and X represents an N-terminal protective group and Y represents a C-terminal protective group.

The proteases recovered by the process of the present invention are proteases used for peptide syntheses.

Suitable proteases include acidic proteases such as pepsin; thiol proteases such as papain, Stembromelein, Ficin, Cathepsin B, Chymopapain and Streptoccal proteases; metallo proteases such as neutral proteases derived from actinomycetes, Prolisin, Thermolysin, Collagenase, Crotulus atrox protease; and serine proteases such as Subtilisin, Aspergillus alkaline proteases, Elastase, α-Lytic protease, Chymotrypsin and Chymotrypsin C.

It is especially suitable to use metallo proteases from the viewpoints of suitable pH range and suitable protease activity in the preparation of the addition compounds.

The first amino acid whose amino group is protected with a protective group can be an amino acid such as asparatic acid, glutamic acid, whose amino group is protected with the protective group such as an aliphatic oxycarbonyl group, benzyloxycarbonyl group which can have substituents on the ring, benzoyl group, an aromatic sulfonyl group or an aromatic sulfinyl group.

Aspartic acid whose amino group is protected with benzyloxycarbonyl group, or alkoxybenzyloxycarbonyl group especially methoxybenzyloxycarbonyl group and glutamic acid whose amino group is protected with said group are especially important as the starting material.

The second amino acid whose carboxyl group is protected with a protective group can be an amino acid such as glycine, alanine, valine, leucine, isoleucine, phenylalanine, methionine, cystine (cysteine) serine, threonine, aspartic acid, glutamic acid, lysine, arginine, histidine, proline, oxyproline, tyrosine and triptophan and whose carboxyl group is protected with the protective group such as an lower alkoxy group, benzyloxy group, benzhydryloxy group, anilino group or amido group.

Monoaminomonocarboxylic acids having no other functional group such as lower alkyl esters of phenylalanine are especially important as the starting material.

The amounts (concentrations) of these starting materials are not critical, and usually the ranges proposed in the prior inventions. For example, these starting materials are used as solutions having each concentration of about 0.001 M to 7 M.

In the prior invention, the ratio of the first starting material to the second starting material is a molar ratio of 1:2.

The molar ratio of the starting materials used in the practical operation is not critical, and usually in a range of about 5:1 to 1:5 preferably about 2:1 to 1:3.

The aqueous medium is usually water. It is possible to combine a water miscible organic solvent if the protease is not precipitated and the precipitation of the reaction product is not prevented by the addition of the water miscible organic solvent.

The amount of the protease can be the same with the amount of the protease used in the prior invention and usually in a range of about 2 to 400 mg ($5 \times 10^{-5}$ to $1 \times 10^{-2}$ mmole) especially 5 to 10 mg ($1 \times 10^{-4}$ to $3 \times 10^{-3}$ mmole) per 1 mmole of the starting material.

The pH of the aqueous medium in the reaction is in a range for imparting the protease activity and imparting the protease activity and performing the formation reaction of the addition compound, usually about 4 to 9.

The reaction temperature is in a range for maintaining the protease activity and preferably about 20° to 50° C.

The reaction time is not critical and preferably about 30 minutes to 24 hours.

In the process of the present invention, the solubility of the addition compound to the aqueous medium is relatively low whereby the reaction product is deposited.

In the case of the prior invention wherein the first component is aspartic acid or glutamic acid whose amino group is protected and the second component is a monoaminomonocarboxylic acid having no other functional group whose carboxyl group is protected with a lower alkoxy group, the precipitates are the addition compounds of the second component with the dipeptide having the first and second components at a molar ratio of 1:1.

When the polar organic solvent which is miscible with water is added to the aqueous medium containing the precipitate, the organic solvent is miscible with the aqueous medium and the precipitate is dissolved. However, the protease is suspended in the resulting solution.

The polar organic solvents which are miscible with water can be alcohols such as methanol, ethanol and propanol; ketones such as acetone; oxygen-containing polar organic solvents such as tetrahydrofuran etc.

The amount of the polar organic solvent is depending upon the solubility to dissolve the precipitate and usually more than 10 wt. parts preferably in a range of 20 to 100 wt. parts per 1 wt. part of the precipitate.

The temperature in the step of dissolving the precipitate by adding the water miscible polar organic solvent is in the range for preventing the deactivation of the protease and usually about −20° to 50° C. preferably about −10° to 30° C.

It is necessary to take care of preventing the freezing of the reaction mixture.

The protease is isolated as the solid phase by suitable solidliquid separation of the resulting suspension.

The solid-liquid separation can be the conventional methods such as the filtration, the centrifugal separation etc.

It is possible to use a filter aid.

The reaction product can be obtained from the isolated liquid phase by the conventional methods for example the method of distilling off the organic solvent and then, extracting it with suitable solvent.

The recovered protease preserves the protease activity whereby it can be used for the peptide synthesis and others.

In accordance with the process of the present invention, the recovery and the reuse of the protease can be attained. The cost of the protease is important for the total cost of the peptide synthesis.

The invention will be further illustrated by certain examples.

EXAMPLE 1:

In a 30 ml flask, 0.534 (2 mmole) of N-benzyloxycarbonyl-L-aspartic acid and 0.863 g (4 mmole) of L-phenylalanine methyl ester hydrochloride were charged and 5 ml of water was added to dissolve them and pH was adjusted to 6.4 with 7% ammonia water.

The resulting solution was admixed with 30 mg of Thermolysin and shaken at 38° to 40° C. for 2.5 hours to react them and 60 ml of acetone was added to the reaction mixture containing the precipitated reaction product which was cooled with ice and the mixture was kept for 40 minutes. The insoluble material was isolated by a centrifugal sedimentation. The protease activity was measured by the casein digestion method. As the result, a relative protease activity of the isolated insoluble material (recovered Thermolysin) to 30 mg of the original Thermolysin was 0.73.

In the following examples, the relative protease activity was measured by the casein digestion method otherwise specified.

On the other hand, acetone was distilled off from the isolated liquid phase at 50° to 60° C. under a reduced pressure and the residue was cooled to the room temperature whereby crystals were deposited.

The crystals were filtered and washed with 10 ml of water and dried to obtain 0.851 g of fine needle-like crystals which was confirmed to be an addition compound of N-benzyloxycarbonyl-L-aspartyl-L-phenylalanine methyl ester and L-phenylalanine methyl ester (1:1) (yield: 70%).

The crystals were recrystallized from a solvent mixture of ethyl acetate and n-hexane. The physical properties and result of elementary analysis of the product were as follows.

Melting point: 120° to 124° C.
$[\alpha]_D^{25}$: +7.1 (C=1, methanol)
Elementary analysis: $C_{32}H_{37}N_3O_9$

|  | C | H | N |
|---|---|---|---|
| Calculated (%) | 63.24 | 6.13 | 6.97 |
| Found (%) | 63.21 | 6.15 | 7.00 |

Infrared and NMR spectra of the product were as follows.

Infrared spectrum:

$3,260^{cm-1}$ (N-H stretching vibration); 3,000 to $3,200^{cm-1}$ (C-H stretching vibration); $1,740^{cm-1}$ (C=O ester); 1,720$cm^{-1}$ (urethane); 1,660$cm^{-1}$ (amide 1st absorption); 1,630$cm^{-1}$ (carboxylate); 1,540$cm^{-1}$ (amide 2nd absorption); 1,430 and 1,450$cm^{-1}$ (C-H deformation vibration); 1,390$cm^{-1}$ (carboxylate); 1,220 to 1,290$cm^{-1}$ (C-O-C stretching vibration and amide 3rd absorption); 1,050$cm^{-1}$ (phenyl in-plane vibration); and 740 and 695$cm^{-1}$ (monosubstituted benzene ring out-of-plane vibration).

NMR spectrum:

δ=2.75 ppm; 3.02 ppm; 3.61 ppm; 3.7 ppm; 4.4–4.8 ppm; 5.05 ppm; 5.82 ppm; 7.3 ppm.

EXAMPLE 2

In accordance with the process of Example 1 except using 3 ml of water for dissolving N-benzyloxycarboxyl-L-aspartic acid and L-phenylalanine methyl ester hydrochloride and using 1N-NaOH aqueous solution for adjusting pH to 6.4 instead of 7% of ammonia water, the reaction and the isolation of the protease were carried out.

The relative protease activity (the casein digestion method) of the recovered Thermolysin to 30 mg of the original Thermolysin was 0.86.

On the other hand, a test sample was prepared by adding L-aspartic acid β-benzyl ester to the filtrate of the acetone solution as the internal standard substance and the yield of the addition compound of N-benzyloxycarbonyl-L-aspartyl-L-phenylalanine methyl ester and L-phenylalanine methyl ester (1:1) was measured by the high speed liquid chromatography analysis to give 60.2%.

The apparatus and conditions in the high speed liquid chromatography analysis are as follows.

Apparatus: High speed liquid chromatography apparatus (TSK-HLC 801 manufactured by Toyo Soda Industrial Co., Ltd.);

Column: Starch gel type: particle size of 5μ. (TSK-GEL LS 170 manufactured by Toyo Soda Industrial Co., Ltd.);

Eluent: 0.5% aqueous solution of sodium acetate;

Flow rate: 0.8 ml/min.;

Pressure loss: 20 Kg/cm$^2$;

Detector: Differential refractometer.

In the following examples, the yields of the products were measured by using the same apparatus under the same condition otherwise specified.

EXAMPLE 3

In a 30 ml flask, 0.534 g (2 mmole) of N-benzyloxycarbonyl-L-aspartic acid and 0.717 g (4 mmole) of L-phenylalanine methyl ester were charged and 7 ml of water was added to dissolved them and pH was adjusted to 6.3 with 7% ammonia water.

The resulting solution was admixed with 30 mg of Thermolysin and the reaction and the isolation of the protease were carried out in accordance with the process of Example 1.

The relative protease activity of the recovered protease to 30 mg of the original Thermolysin was 0.71.

The yield of the addition compound of N-benzyloxycarbonyl-L-aspartyl-L-phenylalanine methyl ester and L-phenylalanine methyl ester (1:1) was 63.7%.

EXAMPLE 4

In accordance with the process of Example 1 except using 53 mg of Thermolysin and reacting them for 2 hours, the reaction and the isolation of the protease were carried out.

The reaction and the isolation were repeated except using the recovered Thermolysin.

The yield of the addition compound of N-benzyloxycarbonyl-L-aspartyl-L-phenylalanine methyl ester and L-phenylalanine methyl ester (1:1) was 82.9% at the first time and 83.7% at the second time.

The relative protease activity of the recovered protease in the second time to 53 mg of the original Thermolysin was 0.73.

EXAMPLE 5

In accordance with the process of Example 1 except dissolving the product with 50 ml of tetrahydrofuran at room temperature instead of 60 ml of acetone cooling with ice, the reaction and the isolation of the protease were carried out. The relative protease activity of the recovered enzyme to 30 mg of the original Thermolysin was 0.59.

The yield of the addition compound of N-benzyloxycarbonyl-L-aspartyl-L-phenylalanine methyl ester and L-phenylalanine methyl ester (1:1) was 67.3%.

EXAMPLE 6

In accordance with the process of Example 1 except reacting for 3 hours and dissolving the product with 40 ml of methanol at 0° C. instead of 60 ml of acetone cooling with ice, the reaction and the isolation of the protease were carried out.

The relative protease activity of the recovered protease to 30 mg of the original Thermolysin was 0.41.

The yield of the addition compound of N-benzyloxycarbonyl-L-aspartyl-L-phenylalanine methyl ester and L-phenylalanine methyl ester (1:1) was 75.4%.

EXAMPLE 7

After the reaction of Example 1, 40 ml of a mixed solvent of methanol and diethyl ether (1:1 by volume) was added to the reaction mixture and the mixture was kept at room temperature for 20 minutes, and the isolation of the protease was carried out in accordance with the process of Example 1.

The relative protease activity of the recovered protease to 30 mg of the original Thermolysin was 0.52.

The yield of the addition compound of N-benzyloxycarbonyl-L-aspartyl-L-phenylalanine methyl ester and L-phenylalanine methyl ester (1:1) was 65.0%.

EXAMPLE 8

In 3 ml of water, 300 mg of Thermoase (titer 1,600,000 PU/g) was dissolved and the insoluble material was separated by the centrifugal sedimentation, and 40 mg of potatoinhibtor was added to 2.0 ml of the supernatant and the mixture was kept for 15 minutes.

In accordance with the process of Example 1 except using the resulting solution instead of 30 mg of Thermolysin, the reaction and the isolation of the protease were carried out.

The reaction and the isolation were repeated except using the recovered protease instead of said solution of the protease.

The yield of the addition compound of N-benzyloxycarbonyl-L-aspartyl-L-phenylalanine methyl ester and L-phenylalanine methyl ester (1:1) was 60.2% at the first time and 68.0% at the second time.

EXAMPLE 9

In accordance with the process of Example 1 except using 50 mg of Thermolysin and dissolving the product with 40 ml of acetonitrile at room temperature instead of 60 ml of acetone by cooling with ice and mixing them for 15 minutes, the reaction and the isolation of the protease were carried out.

The relative protease activity of the recovered protease to 50 mg of the original Thermolysin was 0.68.

The yield of the addition compound of N-benzyloxycarbonyl-L-aspartyl-L-phenylalanine methyl ester and L-phenylalanine methyl ester (1:1) was 69.2%.

EXAMPLE 10

In a 30 ml flask, 0.563 g (2 mmole) of N-benzyloxycarbonyl-L-glutamic acid and 0.863 g (4 mmole) of L-phenylalanine methyl ester hydrochloride were charged and 5 ml of water was added to dissolve them and pH was adjusted to 6.1 with 1 N-NaOH aqueous solution.

The resulting solution was mixed with 50 mg of Thermolysin and the mixture was stirred at 38° to 40° C. for 21 hours to react them and 50 ml of acetone was added to the reaction mixture which was cooled with ice and the mixture was kept for 40 minutes. The insoluble material was isolated by a centrifugal sedimentation. The relative protease activity of the insoluble material to 50 mg of the original Thermolysin was 0.84.

In accordance with the process of Example 1, the isolated acetone solution was treated to obtain 0.806 g (yield 65.0%) of crude crystals of an addition compound of N-benzyloxycarbonyl-L-glutamyl-L-phenylalanine methyl ester and L-phenylalanine methyl ester (1:1).

The physical properties and the result of elementary analysis of the product obtained by recrystallizing from a mixed solvent of ethyl acetate and n-hexane were as follows.

Melting point: 93° to 97° C.
$[\alpha]_D^{25}$: 0.1 (C=1 methanol)
Elementary analysis: $C_{33}H_{39}N_3O_9$

|  | C | H | N |
|---|---|---|---|
| Calculated (%) | 63.75 | 6.32 | 6.75 |
| Found (%) | 63.71 | 6.41 | 6.83 |

Infrared spectrum:

$3,340^{cm-1}$ (N-H stretching vibration); 2,950 and $3,030^{cm-1}$ (C—H stretching vibration); 1,730 and $1,745^{cm-1}$ (C=O ester); $1,690^{cm-1}$ (C=O urethane); $1,660^{cm-1}$ (amide 1st absorption); $1,620^{cm-1}$ (carboxylate); $1,530^{cm-1}$ (amide 2nd absorption); $1,440^{cm-1}$ (C-H deformation vibration); $1,405^{cm-1}$ (carboxylate); 1,240 to $1,310^{cm-1}$ (C-O-C stretching vibration and amide 3rd absorption); $1,050^{cm-1}$ (phenyl in-plane vibration); 700 and $750^{cm-1}$ (phenyl out-of-plane vibration).

NMR spectrum:

δ=2.0 ppm (2H); 2.3 ppm (2H); 3.0 ppm (4H); 3.6 ppm (3H); 3.7 ppm (3H); 3.8 ppm (1H); 4.3 ppm (1H); 4.8 ppm (1H); 5.0 ppm (2H); 5.8 ppm (3H); 5.8 ppm (1H); 7.2 ppm (1H); 7.2 ppm (10H); 7.3 ppm (5H).

EXAMPLE 11

In accordance with the process of Example 1 except using 50 mg of Thermolysin and adding 0.8 g of dextran gel as a filter aid and reacting for 2 hours, the reaction was carried out.

Then, 40 ml of acetone was added to the reaction mixture which was cooled with ice and the mixture was kept for 40 minutes and filtered through a glass filter (G-3) to obtain the insoluble material.

The reaction and the isolation of the protease were repeated except using the insoluble material instead of 50 mg of Thermolysin and 0.8 g of the filter aid.

The yield of the addition compound of N-benzyloxycarbonyl-L-aspartyl-L-phenylalanine methyl ester and L-phenylalanine methyl ester (1:1) was 76.2% at the first time and 57.8% at the second time.

EXAMPLE 12

In accordance with the process of Example 1 except using 50 mg of Thermolysin and reacting for 2 hours, the reaction and the dissolution of the product were carried out.

The resulting mixture was filtered through a glass filter (G-4) and the insoluble material on the glass filter was eluted with 4 ml of water.

The reaction and the isolation of the protease were repeated except using the resulting solution instead of 50 mg of Thermolysin and reacting for 6.5 hours.

The yield of the addition compound of N-benzyloxycarbonyl-L-aspartyl-L-phenylalanine methyl ester and L-phenylalanine methyl ester (1:1) was 51.8% at the first time and 48.2% at the second time.

What is claimed is:

1. A process for recovering protease which comprises reacting a first amino acid whose amino group is protected with a protective group with a second amino acid whose carboxyl group is protected with a protective group in an aqueous medium in the presence of the protease to result in a peptide synthesis and to precipitate the addition compound of a dipeptide and said second C-terminal protected amino acid; dissolving the addition compound into the aqueous medium by adding a polar organic solvent which is miscible with water and separating an insoluble material from the resulting suspension by a solid-liquid separation to isolate the protease as the solid phase.

2. A process according to claim 1 wherein the protective group for the amino group of the first amino acid or peptide is an aliphatic oxycarbonyl group, a benzyloxycarbonyl group which can have ring substituent, a benzoyl group, an aromatic sulfonyl group or an aromatic sulfuryl group; and the protective group for the carboxyl group of the second amino acid or peptide is a lower alkoxy group or benzhydryloxy group.

3. A process according to claim 1 wherein the protease is a metallo protease.

4. A process according to claim 1 wherein the precipitate is the addition compound having the formula

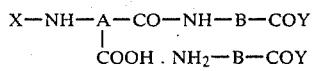

wherein A represents a residue of aspartic acid or glutamic acid excluding C-terminal and N-terminal and B represents a residue of the second amino acid excluding C-terminal and N-terminal and X represents an N-terminal protective group and Y represents a C-terminal protective group.

5. A process according to claim 1 wherein the first amino acid is aspartic acid or glutamic acid and the second amino acid or peptide is a monoaminomonocarboxylic acid having no other functional group.

6. A process according to claim 5 wherein the monoaminomonocarboxylic acid having no other functional group is phenylalanine.

7. A process according to claim 1 wherein the aqueous medium is water.

8. A process according to claim 1 wherein the polar organic solvent is a lower alcohol.

9. A process according to claim 1 wherein the polar organic solvent is acetone.

* * * * *